United States Patent [19]

Subramanyam et al.

[11] Patent Number: 4,526,776
[45] Date of Patent: Jul. 2, 1985

[54] CATIONIC CYANATO AND THIOCYANATO COMPLEXES USEFUL AS RADIODIAGNOSTIC AGENTS

[75] Inventors: Vinayakam Subramanyam, Westwood; Algis Rajeckas, Bedford, both of Mass.

[73] Assignee: E. I. du Pont de Nemours & Company, Wilmington, Del.

[21] Appl. No.: 485,217

[22] Filed: Apr. 15, 1983

[51] Int. Cl.$^3$ ..................... A61K 43/00; A61K 49/00
[52] U.S. Cl. ......................................... 424/1.1; 424/9; 568/2; 568/8; 568/13; 568/14; 568/15; 568/16; 568/17; 534/14
[58] Field of Search ............... 424/1.1, 9; 260/429 R, 260/440, 446; 568/2, 8, 13–17

[56] References Cited

U.S. PATENT DOCUMENTS

| | | | |
|---|---|---|---|
| 2,587,805 | 3/1952 | Akobjanoff | 260/440 |
| 3,188,345 | 6/1965 | Burg et al. | 568/2 |
| 3,478,035 | 11/1969 | Barrett | 564/19 |
| 3,478,036 | 11/1969 | Winkelmann et al. | 564/19 |
| 3,695,853 | 10/1972 | Klanberg | 423/299 |
| 3,798,241 | 3/1974 | Kagan et al. | 260/446 |
| 3,819,670 | 6/1974 | Kemp | 260/440 |
| 4,133,872 | 1/1979 | Schmidt-Dunker et al. | 424/1 |
| 4,247,534 | 1/1981 | Bevan | 424/1 |
| 4,338,248 | 7/1982 | Yokoyama et al. | 424/1 |
| 4,363,793 | 12/1982 | Blau et al. | 424/1 |
| 4,374,821 | 2/1983 | Glavan et al. | 260/429 R |

FOREIGN PATENT DOCUMENTS 0038756 10/1981 European Pat. Off. .............. 424/1

OTHER PUBLICATIONS

Friesen, D. K. et al., J. of Molecular Structure, 31, (1976), 77–95.
Communications to the Editor, J. Am. Chem. Soc., 1980, vol. 102, No. 22, 1980, pp. 6849–6851.
Zsuzsa Nagy-Magos et al., J. of Organometallic Chemistry, 171, (1979), 97–102.
Akhtar, M. et al., Inorganic Chemistry, vol. 11, No. 12, 1972, pp. 2917–2921.
Communications to the Editor, J. Am. Soc., 101, 1979, pp. 1053–1054.
Brown, L. D. et al., Inorganic Chemistry, vol. 17, No. 3, 1978, pp. 729–734.
Albright, J. O. et al., J. Am. Chem. Soc., 101, (1979), 611–619.
Kyba, E. P. et al., J. Am. Chem. Soc., vol. 102, No. 23, 1980, pp. 7012–7014.
Butter, S. A. et al., J. Am. Chem. Soc., (1970), pp. 1411–1415.
Inoue, Y. et al., Bulletin of the Chem. Soc. of Japan, vol. 51(B), (1978), pp. 2375–2378.
Chatt, J. et al., J. Chem. Soc., (1961), pp. 896–904, (1962), pp. 2545–2549.
Mazzi, U. et al., Inorganic Chemistry, vol. 16, No. 5, 1977, pp. 1042–1048.
Ferguson, J. E. et al., Aust. J. Chem., 1970, 23, 453–61.
King, R. B., Acc. Chem. Res., 1980, 13, pp. 243–248.
Curtis, N. F., Chemistry and Industry, May 24, 1958, pp. 625–626.
Communications to the Editor, J. Am. Chem. Soc., 97, (1975), pp. 1955–1956.
Bandoli, G. et al., J. C. S. Dalton, (1976), pp. 125–130.
Wymore, C. E. et al., J. Inorg. Nucl. Chem., 1960, vol. 14, pp. 42–54.
Ferguson, J. E. et al., J. Inorg. Nucl. Chem., 1966, vol. 28, pp. 2293–2296.
Cooper, P. et al., J. Chem. Soc., (C) (1971), pp. 3031–3035.
Subramanian, Gopal et al., Proceedings of the 28th Annual Meeting, Los Vegas, Jun. 16–19, 1981, vol. 22, No. 6, p. 51.
Deutsch, E. et al., Science, vol. 214, (1981), pp. 85–86.
Ferguson, J. E. et al., Chemistry and Industry, Nov. 22, 1958, p. 1555.
Viard, B., J. Inorg. Nucl. Chem., 1977, vol. 39, pp. 1090–1092.
Fergusson et al., Chemistry and Industry, pp. 347, 348.
Deutsch et al, J. Nucl. Med., vol. 22, (Oct. 1981); 897–907.

Primary Examiner—Christine M. Nucker
Attorney, Agent, or Firm—Sewall P. Bronstein; George W. Neuner

[57] ABSTRACT

An hepatobiliary imaging agent is disclosed which is a cationic complex of Tc-99m, a cyanate or thiocyanate ion, and a mono or polydentate organic ligand having one or more donor atoms, each with a free-electron pair available for accepting a proton or for complexing with Tc-99m to form a cationic complex. These complexes can provide images of the hepatobiliary transit in as little as ten minutes.

35 Claims, No Drawings

CATIONIC CYANATO AND THIOCYANATO COMPLEXES USEFUL AS RADIODIAGNOSTIC AGENTS

FIELD OF THE INVENTION

The present invention relates to cationic radiodiagnostic agents and, in particular, to novel $^{99m}$Tc-labelled cationic cyanato and thiocyanato radiodiagnostic agents, kits for preparing such $^{99m}$Tc-labelled cationic cyanato and thiocyanato radiodiagnostic agents, and methods for using such $^{99m}$Tc-labelled cationic cyanato thiocyanato radiodiagnostic agents.

BACKGROUND OF THE INVENTION

Various complexes of monodentate and bidentate ligands with technetium have been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347–8 (March26, 1960); *J. Inorg. Nucl. Chem.*, Vol. 28, pp 2293–96 (1966); *Aust. J. Chem.*, 23, pp 453–61 (1970); *Inorganic Chem.*, Vol. 16, No. 5, pp. 1041–48 (1977); *J. Inorg. Nucl. Chem.*, Vol. 39, pp. 1090–92 (1977); and *J. C. S. Dalton*, pp. 125–30 (1976).

In a presentation to the American Pharmaceutical Association, E. A. Deutsch disclosed that certain complexes of DIARS, i.e.

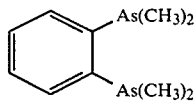

I and Tc-99m, and certain complexes of DMPE, i.e. $(CH_3)_2PCH_2CH_2P(CH_3)_2$ and Tc-99m, may be useful as radiodiagnostic agents for myocardial or hepatobiliary imaging. $[^{99m}Tc\text{-}(DMPE)_2Cl_2]+$ and $[^{99m}Tc\text{-}(DIARS)_2Br_2]+$ were prepared by Deutsch by heating in an open flask a reaction mixture containing the appropriate hydrogen halide in aqueous alcohol solution, $^{99m}$Tc-sodium pertechnetate, and ortho-phenylenebis(dimethylarsine), i.e. DIARS, or bis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a skilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}$Tc-labelled complex make the Deutsch procedure undesirable.

Certain commercially available hepatobiliary imaging agents, such as $^{99m}$Tc-labelled disofenin, take up to thirty (30) minutes to obtain an image of the hepatobiliary transit. It is desirable to have hepatobility agents with faster blood clearance rates that would enable the visualization of the hepatobiliary transit in less time.

SUMMARY OF THE INVENTION

The present invention provides a new hepatobiliary transit imaging agent that provides usable visible images in as little as ten minutes. The new hepatobiliary imaging agent is a cationic complex of Tc-99m, a cyanate or thiocyanate ion, and a mono or polydentate organic ligand having one or more donor atoms, each with a free-electron pair available for accepting a proton or for complexing with Tc-99m to form a cationic complex.

The present invention also provides a kit for making a hepatobiliary imaging agent wherein the kit preferably contains a water soluble cyanate or thiocyanate salt and a water soluble salt of a mono or polydentate organic ligand having one or more donor atoms, each with a free-electron pair available for accepting a proton or for complexing with Tc-99m to form a cationic complex. Preferably, these salts are contained in a sterile container or vial.

The hepatobiliary imaging agent kit is used by adding $^{99m}$Tc-sodium pertechnetate to the salts to form a cationic complex. Typically, the complex is formed at elevated temperatures (above room temperature). However, the temperature may be reduced if accelerators are used to aid in forming the complex.

The hepatobiliary imaging agent of this invention is used by injecting the cationic complex intravenously into a mammal, and positioning the mammal under a scintillation camera to obtain images of the hepatobiliary transit.

DETAILED DESCRIPTION OF THE INVENTION

The cationic cyanato- and thiocyanato-technetium complexes of the present invention are preferably made by admixing the organic ligand, the thiocyanate ion and $^{99m}$Tc-sodium pertechnetate in a liquid carrier at a pH greater than about 3.5, preferably in the range between 3.5 and 5.5 and heating the admixture above room temperature for a period of time to cause the formation of a cationic complex of the ligand, cyanate or thiocyanate ion and Tc-99m.

Organic ligands useful in the practice of the present invention include those having the following structural formulas:

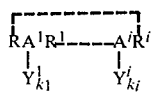

II wherein:
 i is an integer from 1 to 6;
 R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polycycloalkyl, heterocyclic and carbocyclic groups;

$A^1$, $A^2$, $A^3$, $A^4$, $A^5$ and $A^6$ are the sme or different donor atoms, each having a free-electron pair available for accepting a proton to provide a charged ligand or for complexing with Tc-99m or Tc-99 to form a cationic complex; and $k_1$, $k_2$, $k_3$, $k_4$, $k_5$ and $k_6$ are each independently zero or one;

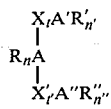   III wherein:

R, R' and R" are independently selected from hydrogen or substituted or unsubstituted alkyl, aryl, alkylaryl, arylalkyl, monocycloalkyl, polycycloalkyl, heterocyclic and carbocyclic groups;

A, A' and A" are independently selected from the group of donor atoms having a pair of electrons available for accepting a proton to provide a charged ligand or for complexing with Tc-99m or Tc-99 to form a cationic complex; and X and X' are saturated or unsaturated alkyl groups;

n, n' and n" are independently the integer 1 or 2;

t and t' are independently 0 or 1; or

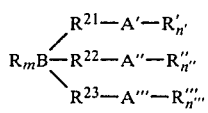   IV wherein:

R', R", and R'" are each independently selected from hydrogen or substituted or unsubstituted alkyl, aryl, alkylaryl, arylalkyl, monocycloalkyl, polycycloalkyl, heterocyclic and carbocyclic groups;

A', A" and A'" are independently selected from the group of donor atoms having a pair of electrons available for accepting a proton to provide a charged ligand complexing with Tc-99m or Tc-99 to form a cationic complex;

B is an atom selected from the group of donor atoms having a pair of electrons for complexing with Tc-99m or Tc-99, boron or from the elements listed in Group IV A of the periodic table (i.e. C, Si, Ge, Sn, and Pb);

m is 0 or 1;

n', n", and n'" are independently the integer 1 or 2.

The R's and X's in formulas (II), (III) and (IV) are preferably alkyl radicals having 1 to about 6 carbon atoms such as methyl, ethyl, etc., and the like, and aryl radicals having 1 to about 6 carbon atoms such as methyl, ehtyl, etc., and the like, and aryl radicals such as benzyl, phenyl, etc., and the like. When more than one R group is attached to the same donor atom, the R groups so attached can be the same or different. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

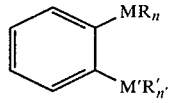   V in which M and M' are arsenic, phosphorus, nitrogen, sulfur, oxygen, selenium, tellurium, or any combination of them, n and n' are independently 1 or 2 depending upon the particular donor atom used for M and M', and R and R' are independently hydrogen, or an organic group, preferably an alkyl group having 1 to 6 carbon atoms, an aryl group such as phenyl, or the like, and substituted such groups. Additional examples of suitable ligands include bidentate cis-tetraethylene ligands of the formula:

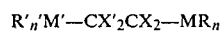   VI in which M, M', R, and R' are as defined above, n and n' are independently 1 or 2 depending upon the particular donor atom used for M and M', and X and X' are independently selected from hydrogen, halide, or substituted or unsubstituted lower alkyl groups having 1 to about 6 carbon atoms. Further examples of suitable ligands include those having the formula:

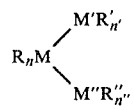   VII where M, M', R, and R', are as defined above, M" is independently selected from arsenic, phosphorous, nitrogen, sulfur, oxygen, selenium, and tellurium, and n is 0 or 1, n' and n" are independently 0, 1 or 2, and R" is independently selected from hydrogen, halide or an organic radical, preferably an alkyl radical having 1 to about 6 carbon atoms, an aryl radical such as phenyl, or the like, and substituted such groups.

Particularly preferred ligands for the practice of this invention are the bis-dialkylphosphinoethanes and their substituted derivatives, including, for example, 1,2-bis(dimethylphosphino)ethane,
1,2-bis(di(trifluoromethyl)phosphino)ethane,
1,2-bis(dimethylphosphino)-1,1-difluoroethane,
1,2-bis(dimethylphosphino)-1-fluoroethane,
1,2-bis(dimethylphosphino) propane,
1,2-bis(di(trifluoromethyl)phosphino)-1,1,2,2-tetrafluoroethane,
1,2-bis(di(trifluoromethyl)phosphino)propane,
2,3-bis(di(trifluoromethyl)phosphino)butane,
1,2-bis(di(trifluoromethyl)phosphino)butane,
1,3-bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane, and
similar compounds wherein the phosphorus is replaced by nitrogen, arsenic, sulfur, oxygen, selenium, tellurium, or another atom having a free electron pair, and the like.

Other useful ligands include the alkylaminobis(diflurorphosphine), i.e., $RN(PF_2)_2$, ligands and the like where R is an organic group, preferably an alkyl group having 1 to about 6 carbon atoms, an aryl group as phenyl, or the like, and substituted such groups; and the o-phenylene compounds such as, for example, orthophenylenebis(diarsine), orthophenylenebis(dimethylarsine), orthophenylenebis(diamine), orthophenylenebis(dimethylamine), orthophenylenebis(diphosphine), orthophenylenebis(dimethylphosphine), and the like.

Additional ligands suitable for use in the present invention are those described by Nuzzo et al., in *J. Amer. Chem. Soc.*, 101, p. 3683 (1979) and by Wilson et al., *J. Amer. Chem. Soc.*, 100, p. 2269 (1978), which are hereby incorporated by reference.

Any donor element can be used in the ligand in accord with this invention provided that it is an atom having a free-electron pair available for accepting a proton to provide a charged ligand and further provided that it has the capability of complexing with technetium (Tc-99 or Tc-99m) to form a cationic complex in the presence of suitable anions. Suitable such elements include, for instance, phosphorous (P), arsenic (As), nitrogen (n), oxygen (O), sulfur (S), antimony (Sb), selenium (Se), tellurium (Te), and the like. Preferred elements are P and As.

The organic ligands described above are preferably used in the form of a water-soluble ligand acid salt, such as described in copending application Ser. No. 311,770 filed on Oct. 15, 1981 in the name of Vinayakam Subramanyam, which is incorporated herein by reference.

The cationic technetium complexes useful for radiodiagnostic treatments can be prepared by mixing in an aqueous or alcoholic solution the organic ligand or its acid salt and $^{99m}$Tc-pertechnetate in the presence of a cyanate or thiocyanate anion and heating the mixture to form the cationic complex. Alternatively, an intermediate complex can be formed by mixing the organic ligand or its acid salt with $^{99m}$Tc-pertechnetate in the presence of a suitable complex formation assisting anion, such as a halide ion, and heating the mixture to form the intermediate complex. Then, the cyanate or thiocyanate anion is added to the mixture, for instance in the form of its potassium salt, and the mixture is heated to form the $^{99m}$Tc-cyanate-ligand complex or $^{99m}$Tc-thiocyanate-ligand complex of this invention.

Although not wishing to be bound by any theory, it is believed that the cyanate anion, NCO—, can form coordinate bonds with the $^{99m}$Tc through either the oxygen or nitrogen atom and that the particular compound formed depends upon the reaction conditions. Correspondingly the thiocyanate anion NCS—, can form bonds through either the sulfur or nitrogen atom. Certain conditions will favor one product over the other.

Accelerator compounds can be used in the practice of the present invention to lower the temperature and/or reduce the time required to form the cationic complexes. Such accelerator compounds can be selected from the group of bidentate ligands capable of forming a four to six, preferably five member chelate ring with technetium. Preferably, such bidentate ligands also have the capability of reducing technetium. Bidentate ligands suitable as accelerators for the practice of this invention include dicarboxylic acids, diphosphonic acids, enols, acidic 1,2-dihydroxy compounds, particularly 1,2-dihydroxy compounds having a nearby strongly electron-withdrawing group, alpha-hydroxycarboxylic acids, alpha-hydroxyphosphonic acids, and the like, etc. Specific examples of such accelerators include, for instance, catechol, oxalic acid, ascorbic acid, tartaric acid, hydroxymethylenediphosphonic acid, methylene diphosphonic acid, and the like, etc. Examples of electron-withdrawing groups suitable for use in such 1,2-dihydroxy compounds are —$NO_2$, —Cl, —Br, —F, —I, or —$CF_3$. Such accelerator compounds are more fully described in copending application Ser. No. 341,553 filed Jan. 22, 1982 in the name of Michael F. Tweedle, which is hereby incorporated by reference.

Preferably the organic ligand and the cyanate or thiocyanate ion are provided as salts or lyophilized compositions in a kit, such as a presterilized vial. The presterilized vial, such as a glass vial, containing the organic ligand and the cyanate or thiocyanate salt is ready for use for preparing cationic technetium complexes for radiodiagnostic use. Of course, the ligand can be in one vial and the cyanate or thiocyanate salt in a second vial, if so desired. More preferably, the organic ligand and cyanate or thiocyanate salt are lyophilized in such kits to increase storage stability of the compositions. In such lyophilized kits, the organic ligand is generally present as a water-soluble acid salt of the ligand.

The pertechnetate solution can then be injected into the vial under aseptic conditions to maintain sterility. The vial is generally heated and maintained at an elevated temperature for sufficient time to form a complex of the ligand cyanate ion with technetium. The vial should be heated to at least 80° C. or more, and more preferably to a temperature in the range of from about 130° C. to about 150° C. At about 150° C., the reaction can be completed in about five to ten minutes, depending upon the choice and concentrations of the reactants.

Kits for the preparation of the cationic technetium complex can also include a polyhydroxy-compound. The use of the polyhydroxy-compound, for reasons not fully understood, results in a more consistent yield of the cationic technetium complex. Preferred polyhydroxy-compounds include, for example, Hetastarch (hydroxyethyl starch), mannitol, glycerol, D-mannose, sorbitol, and the like.

The organic ligand and cyanate or thiocyanate salt for making cationic hepatobiliary complexes of the present invention are preferably supplied in a radiopharmaceutical preparation kit comprising a sterilized unit (or multiple) dose vial containing the purified organic ligand acid salt and cyanate or thiocyanate salt. About 50 mCi or $^{99m}$Tc-pertechatate in saline is injected aseptically into the unit dose vial and the mixture heated to form the labelled cationic complex. After cooling, the resulting radiopharmaceutical preparation may be adjusted for pH and is ready for use. Typically, when the pH is adjusted, it is adjusted into the range of from about 4.0 to about 9.0, and preferably to physiological pH.

To image the hepatobiliary transit of a mammal, a radiopharmaceutical preparation in accord with the invention, having a suitable quantity of radioactivity for the particular mammal, is injected intravenously into the mammal. The mammal is positioned under a scintillation camera in such a way that the hepatobiliary system is covered by the field of view. High quality images are obtained analogous to those seen in clinical studies using Disofenin.

This invention will be further illustrated by the examples that follow:

Preparation of 1,2-Bis(dimethylphosphino)ethane bis-bisulfate, i.e. $DMPEH_2^{2+}.2HSO_4^-$ or $DMPE.2H_2SO_4$ Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml. of methanol. Filter and dry under vacuum. 920 mg of a crystalline solid is obtained, which melts at 135°–136.5° C. Structure and purity of the compound DMPE-bis(bisulfate) was confirmed by its infra-red and nuclear magnetic resonance spectra and elemental analysis.

Preparation of - $DMPE.2H_2SO_4$ Kit

Dissolve 5 g mannitol and 230 mg DMPE-bis(bisulfate) as prepared above in about 35 ml low-oxygen distilled water, and adjust the pH of the solution to 1.0 with 3 N sulfuric acid. Under cover of nitrogen, and with stirring, add low-oxygen distilled water gravimetrically, to a solution weight of 50 g. Dispense 1 ml of this solution into each of several 10 cc vials. Freeze-dry in keeping with procedures well-known to those skilled in the art, stoppering under nitrogen.

PREPARATION OF - $^{99m}TC$-Labelled DMPE

Inject 50 mCi of $^{99m}Tc$-pertechnetate in 0.5 ml physiological saline into each vial of $DMPE.2H_2SO_4$ as prepared above and place it in a steam autoclave preheated to 100° C. Set the temperature control to 135° C., and when that temperature is achieved, maintain it for 20 minutes. Allow the system to cool to 100° C. and remove the vial. HPLC analyses, show a yield of 95 to 100% of the $^{99m}Tc$-labelled DMPE.

EXAMPLE 1

Preparation of $^{99m}Tc$-Thiocyanato - DMPE Complexes

To a $^{99m}Tc$-labelled DMPE preparation is added 0.3 ml 0.5N sodium hydroxide containing 25 mg potassium thiocyanate. After heating 30 minutes in a boiling water bath, HPLC analyses shows a labelled thiocyanato complex which has cationic characteristics by electrophoresis.

EXAMPLE 2

Alternative Preparation of $^{99m}Tc$-Thiocyanato - DMPE Complex

To the freeze-dried (but not as yet labelled) preparation of $DMPE.2H_2SO_4$ as described above is added 1 ml of physiological saline containing 10–20 mCi $^{99m}Tc$-pertechnetate and 0.3 ml 0.5N sodium hydroxide containing 25 mg potassium thiocyanate. After autoclaving for 30 minutes at 135° C. HPLC analysis reveals a labelled complex distinguishable from the thiocyanato complex of Example 1, but which has similar cationic characteristics by electrophoresis.

EXAMPLE 3

Visualization of Hepatobiliary Transit with $^{99m}Tc$-labelled Disofenin (Prior Art)

A lyophylized vial of HEPATOLITE ™ (New England Nuclear Corporation's brand of Technetium Tc99m Disofenin) is labelled with $^{99m}Tc$-pertechnetate in accordance with manufacturer's directions. At least 1 mCi of the labelled preparation is injected intravenously into a 2.5 Kg male New Zealand Albino rabbit. The rabbit is positioned under a Searle Pho-Gamma scintallation camera in such a way that the liver and gastrointestinal tract are within the field of view. Sequential images taken from the time of injection demonstrate an initial liver uptake with gradual visualization of the gall bladder and gastro-intestinal tract, analogous to the diagnostically efficacious results obtained in clinical studies of normal healthy humans.

EXAMPLE 4

Visualization of Hepatobiliary Transit with $^{99m}Tc$-Thiocyanato-Complexes

Greater than 1 mCi of the $^{99m}Tc$-Thiocyanato-DMPE complex from either Example 1 or 2 is injected into a rabbit as in Example 3. Sequential images of hepatobiliary transit reveal rapid passage and comparable image quality of the liver, gall bladder and gastro-intestinal tract in about 10 minutes as compared to about 30 minutes for Disofenin.

This invention has been described in detail with particular reference to the preferred embodiments thereof. However, it will be appreciated that those skilled in the art, upon reading this disclosure, may make modifications and improvements within the spirit and scope of the invention.

We claim:

1. A composition for providing a cationic organic ligand-cyanato-technetium or organic ligand-thiocyanato-technetium complex, said composition comprising (1) a cyanate or thiocyanate ion and (2) a mono- or polydentate organic ligand having one or more donor atoms, each with a free-electron pair available for accepting a proton or for complexing with technetium to form a cationic complex, said organic ligand and said cyanate or thiocyanate ion forming said cationic organic ligand-cyanato-technetium complex or organic ligand-thiocyanato-technetium complex, respectively, when reacted with technetium.

2. A kit comprising the composition of claim 1 and having a first vial containing said organic ligand and a second vial containing said cyanate or thiocyanate ion.

3. A kit in accord with claim 2 wherein said organic ligand is present in the form of a lyophilized acid salt.

4. A kit in accord with claim 3 wherein said lyophilized acid salt and a cyanate or thiocyanate ion in solid form are present in one vial.

5. A kit in accord with claim 4 wherein said vial and its contents are sterilized.

6. A kit in accord with claim 3 wherein said ligand acid salt is a normally solid, hydrophilic compound capable of binding with Tc-99m to form a cationic complex and having a formula selected from:

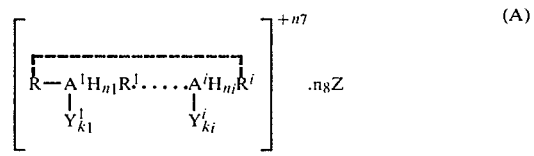

(A)

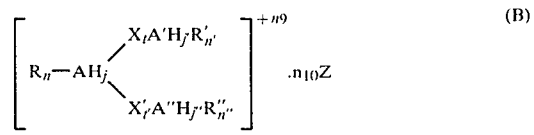

(B)

or

-continued

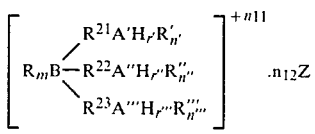

wherein:
R, R', R", R''', R¹, R², R³, R⁴, R⁵, R⁶, R²¹, R²² and R²³ are each independently selected from hydrogen; or substituted or unsubstituted alkyl, alkylene, aryl, alkylaryl, arylalkyl, monocycloalkyl, polycycloalkyl, heterocyclic and carbocyclic group; and R plus $R^i$ in formula (A) may be taken together to form a cyclic compound;
A, A', A", A¹, A², A³, A⁴, A⁵ and A⁶ are independently selected donor atoms, each having a free electron pair available for accepting a proton to provide a charged ligand and having the capability of complexing with Tc-99m to form a cationic complex;
B is an atom selected from the group of donor atoms having a pair of electrons for complexing with Tc-99m or Tc-99, boron or from the elements listed in Group IV A of the periodic table;
Y¹, Y², Y³, Y⁴, Y⁵ and Y⁶ are each independently selected from hydrogen; or substituted or unsubstituted alkyl, alkylene, aryl, alkylaryl, arylalkyl, monocycloalkyl, polycycloalkyl, heterocyclic and carbocyclic groups;
X and X' are saturated or unsaturated alkyl groups;
Z is an anion;
i is an integer from 1 to 6;
j, j' and j" are each independently 0 or 1;
k¹, k², k³, k⁴, k⁵ and k⁶ are each independently 0 or 1;
n, n' and n" are each independently the integer 1 or 2;
$n_1$, $n_2$, $n_3$, $n_4$, $n_5$, $n_6$, are independently 0 or 1;
$n_7$ and $n_8$ are each an integer from 1 to 6;
$n_9$, $n_{10}$, $n_{11}$ and $n_{12}$ are each an integer from 1 to 3;
m is 0 or 1;
r', r" and r''' are independently 0 or 1; and
t and t' are independently 0 or 1.

7. The kit of claim 6 having the formula:

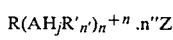

wherein R is ethyl or phenyl, A is phosporous or arsenic, and R' is a lower alkyl group having from 1 to about 6 carbon atoms.

8. The kit of claim 7 wherein Z is bisulfate, biphosphate, or tetrafluoroborate.

9. The kit of claim 6 wherein Z is derived from sulfuric acid, phosphoric acid, perchloric acid, nitric acid or boric acid.

10. The kit of claim 6 wherein A is selected from the group consisting of P, As, N, O, S, Sb, Se and Te.

11. The kit of claim 6 wherein said ligand acid salt has the formula:

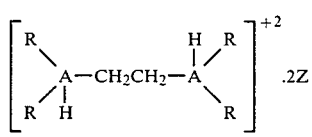

wherein

A is P or As; and
each R is independently H, a lower alkyl group having from 1 to about 6 carbon atoms, or phenyl.

12. The kit of claim 11 wherein Z is bisulfate, biphosphate, nitrate, tetrafluoroborate or perchlorate.

13. The kit of claim 11 wherein A is phosphorus.

14. The kit of claim 11 wherein A is phosphorous and R is methyl or ethyl.

15. The kit of claim 11 having the formula:

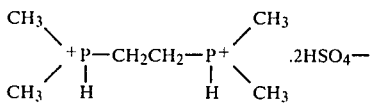

16. The kit of claim 6 wherein said ligand acid salt has the formula:

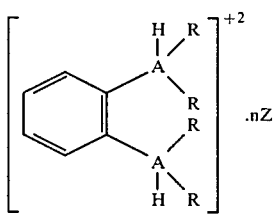

wherein A is P or As; and each R is independently H, or a lower alkyl group having from 1 to about 6 carbon atoms.

17. The kit of claim 16 wherein Z is bisulfate, biphosphate, nitrate, tetrafluoroborate or perchlorate.

18. The kit of claim 16 wherein A is phosphorous.

19. The kit of claim 16 wherein A is phosphorus and R is methyl or ethyl.

20. The kit of claim 16 having the formula:

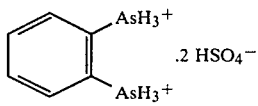

21. A kit in accord with claim 1 further comprising an accelerator.

22. A method for making a cationic hepatobiliary radiodiagnostic agent, and method comprising reacting sodium pertechnetate with (a) an organic ligand having one or more donor atoms, each with a free-electron pair available for accepting a proton or for complexing with technetium to form a cationic complex and (b) a cyanate or thiocyanate ion, thus forming said cationic hepatobiliary agent.

23. The method in accord with claim 22 wherein said reacting step is carried out at a pH in the range of about 3.5 to 5.5.

24. The method in accord with claim 22 wherein said reacting step includes heating the reaction mixture.

25. The method in accord with claim 22 wherein said reacting step includes admixing said sodium pertechetate, organic ligand and said cyanate or thiocyanate ion, and then heating said admixture.

26. The method in accord with claim 25 wherein said admixing step includes adjusting the pH in the range of about 3.5 to 5.5.

27. The method in accord with claim 22 wherein said reacting step includes (1) admixing said pertechnetate and said organic ligand in the presence of a halide ion to form an intermediate complex and (2) admixing a cyanate or thiocyanate ion with said intermediate complex and further heating to form a cyanato-technetium-ligand complex or a thiocyanato-technetium-ligand complex, respectively.

28. The method in accord with claim 27 wherein said second admixing step includes adjusting the pH in a range of about 3.5 to 5.5.

29. A cationic hepatobiliary radiodiagnostic agent made by reacting sodium pertechnetate with (a) an organic ligand having one or more donor atoms, each with a free-electron pair available for accepting a proton or for complexing with technetium to form a cationic complex and (b) a cyanate or a thiocyanate ion.

30. The radiodiagnostic agent in accord with claim 29 wherein said reacting step is carried out at a pH in the range of about 3.5 to 5.5.

31. The radiodiagnostic agent in accord with claim 29 wherein said reacting step includes heating the reaction mixture.

32. The radiodiagnostic agent in accord with claim 29 wherein said reacting step includes admixing said sodium pertechnetate, said organic ligand and said cyanate or thiocyanate ion, and then heating said admixture.

33. The radiodiagnostic agent in accord with claim 32 wherein said admixing step includes adjusting the pH in the range of about 3.5 to 5.5.

34. The radiodiagnostic agent in accord with claim 29 wherein said reacting step includes (1) admixing said pertechnetate and said organic ligand in the presence of a halide ion to form an intermediate complex and (2) admixing a cyanate or thiocyanate ion with said intermediate complex and further heating to form a cyanato-technetium-ligand complex or a thiocyanato-technetium-ligand complex, respectively.

35. The radiodiagnostic agent in accord with claim 34 wherein said second admixing step includes adjusting the pH in a range of about 3.5 to 5.5.

* * * * *